United States Patent [19]
Hall et al.

[11] Patent Number: 5,969,787
[45] Date of Patent: Oct. 19, 1999

[54] EYEWEAR WITH BROWBAR VENTILATION AND DETACHABLE TEMPLES

[75] Inventors: James Hall, Lincoln, R.I.; Raoul O. Desy, Sturbridge; Muthuswamy Ethirajan, Southbridge, both of Mass.

[73] Assignee: Cabot Safety Intermediate Corporation, Newark, Del.

[21] Appl. No.: 09/095,861

[22] Filed: Jun. 11, 1998

[51] Int. Cl.⁶ .................................................. G02C 11/08
[52] U.S. Cl. .......................................... 351/62; 351/110
[58] Field of Search .................................. 351/62, 83, 86, 351/103, 106, 108, 110, 41, 111, 118, 119, 44, 80

[56] References Cited

U.S. PATENT DOCUMENTS

| | | |
|---|---|---|
| 2,584,934 | 2/1952 | Splaine ........................................ 351/62 |
| 2,608,687 | 9/1952 | Ellis ............................................ 351/62 |
| 4,877,320 | 10/1989 | Holden . |
| 5,576,775 | 11/1996 | Bolle . |
| 5,638,145 | 6/1997 | Jannard et al. . |

*Primary Examiner*—Hung Xuan Dang
*Attorney, Agent, or Firm*—Cantor Colburn LLP

[57] ABSTRACT

A ventilated browbar fame and eyewear utilizing the same. The browbar frame is detachably secured to a lens and temples are detachably secured to the browbar frame. The browbar frame includes a plurality of openings to allow air to pass through the browbar frame thereby preventing fogging of the lens. The temples are pivotally attached to the browbar frame to allow for adjustment of the pantoscopic angle of the eyewear.

25 Claims, 5 Drawing Sheets

1

EYEWEAR WITH BROWBAR VENTILATION AND DETACHABLE TEMPLES

FIELD OF THE INVENTION

This invention relates generally to eyewear. More particularly, this invention relates to eyewear frames for use in safety and recreational (e.g., sports) applications and the eyewear (e.g., spectacles) made from such frames.

BACKGROUND OF THE INVENTION

FIG. 1 is a perspective view of conventional protective eyewear shown generally at 100. Eyewear 100 includes a browbar frame 102 which receives lens 104. Temples 106 are hingedly attached to the distal ends of browbar frame 102. Although the conventional protective eyewear 100 is well suited for its intended purpose, there are drawbacks to the conventional design. One potential problem with prior art protective eyewear 100 is that fogging of lens 104 can occur because of the close fit of the browbar frame 102 to the wearer's face thereby trapping warm, moist air. Another drawback is that the temples 106 cannot be adjusted to vary the pantoscopic angle of the eyewear.

SUMMARY OF THE INVENTION

The above-discussed and other problems and deficiencies of the prior art are overcome or alleviated by the ventilated browbar frame of the present invention. In accordance with the present invention, the eyewear is comprised of a browbar frame, a lens and temples pivotally connected to the browbar frame all of which are detachably connected together for easy assembly. In a preferred embodiment, a lens is selected and sized to snaplockedly engage the browbar frame. The two temple assemblies are pivotally coupled to browbar attachment segments to allow for adjusting the pantoscopic angle of the eyewear. The preferred lens has side shields that snaplockedly engage the browbar frame. The browbar frame includes a plurality of ventilation holes to preclude fogging of the lens.

The above-discussed and other features and advantages of the present invention will be appreciated and understood by those of ordinary skill in the art from the following detailed description and drawings.

BRIEF DESCRIPTION OF THE DRAWINGS

Referring now to the FIGURES, wherein like elements are numbered alike in the several FIGURES.

DESCRIPTION OF THE PREFERRED EMBODIMENT

Figure 1:
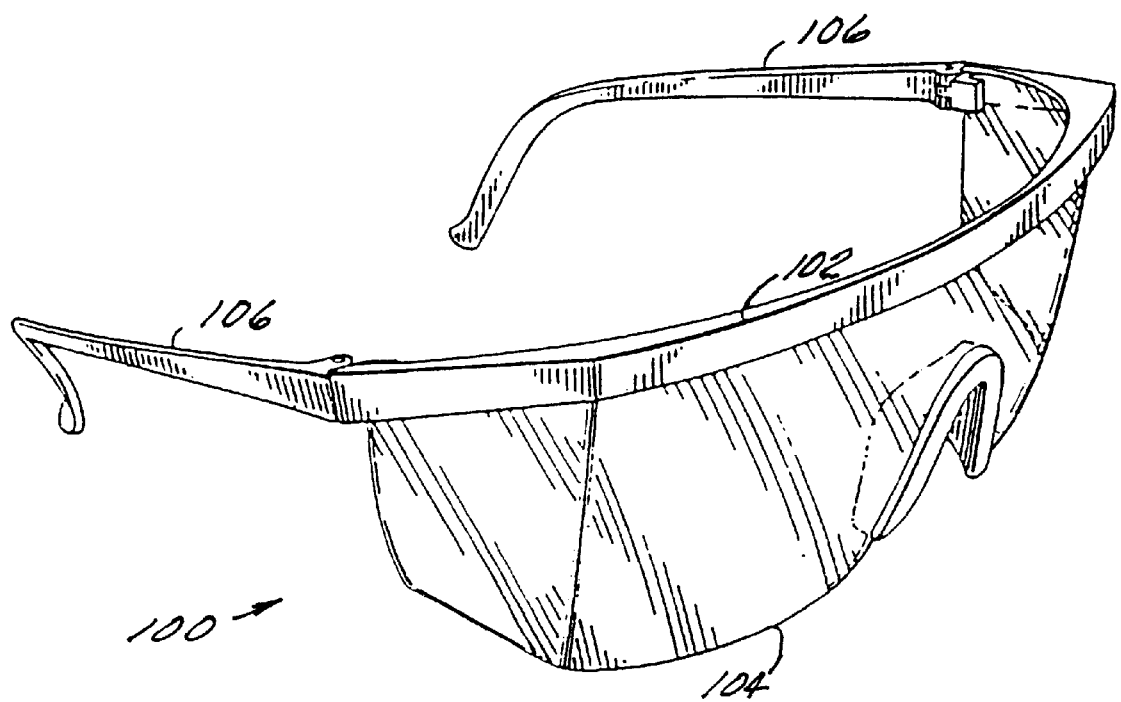
FIG. 1 is a perspective view of conventional eyewear.
Figure 2:
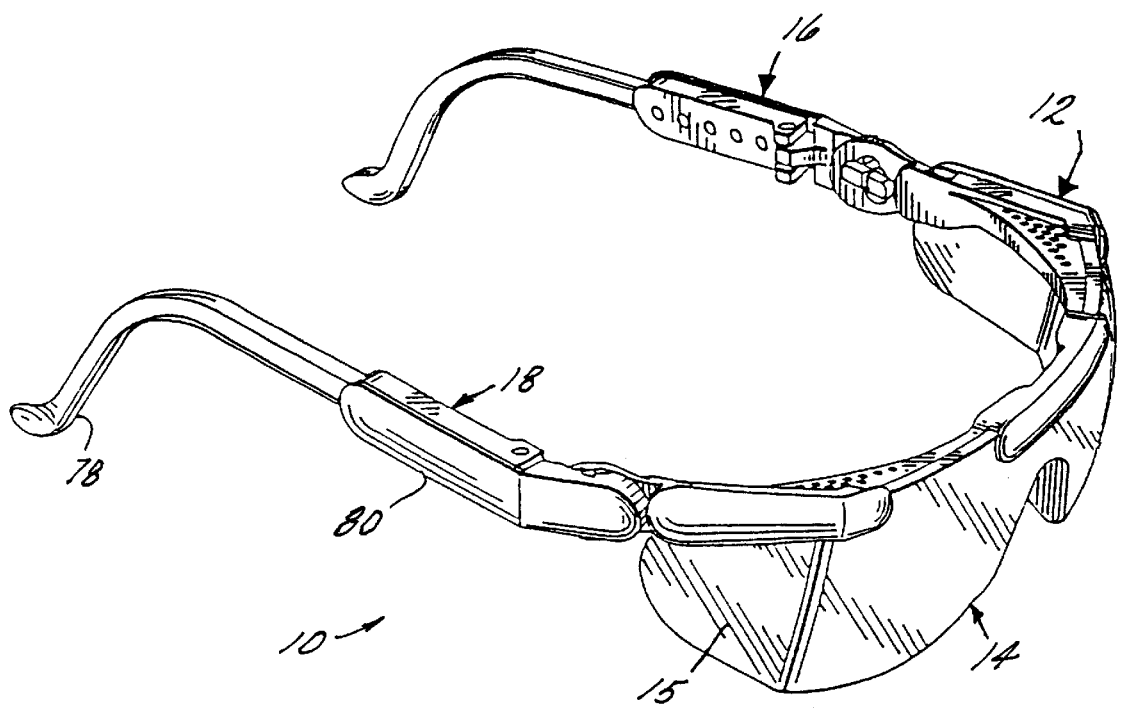
FIG. 2 is a perspective view of the preferred embodiment of the eyewear incorporating the ventilated browbar frame in accordance with the present invention.
Figure 4:
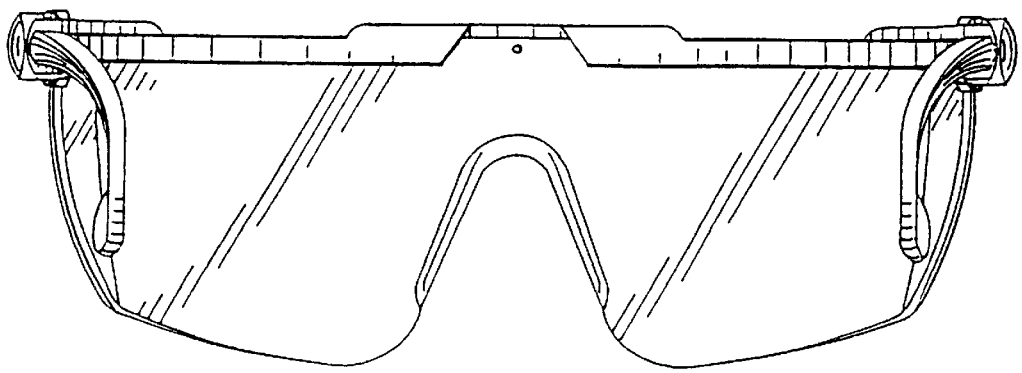
FIG. 4 is a rear view of the eyewear.

Referring first to FIG. 2, eyewear including a ventilated browbar frame with pivotal, adjustable temples of the present invention is shown generally at 10. Eyewear 10 is comprised of a ventilated browbar frame 12, a suitable optical quality lens 14 and two pivotal, adjustable temple assemblies 16 and 18.

Figure 3:
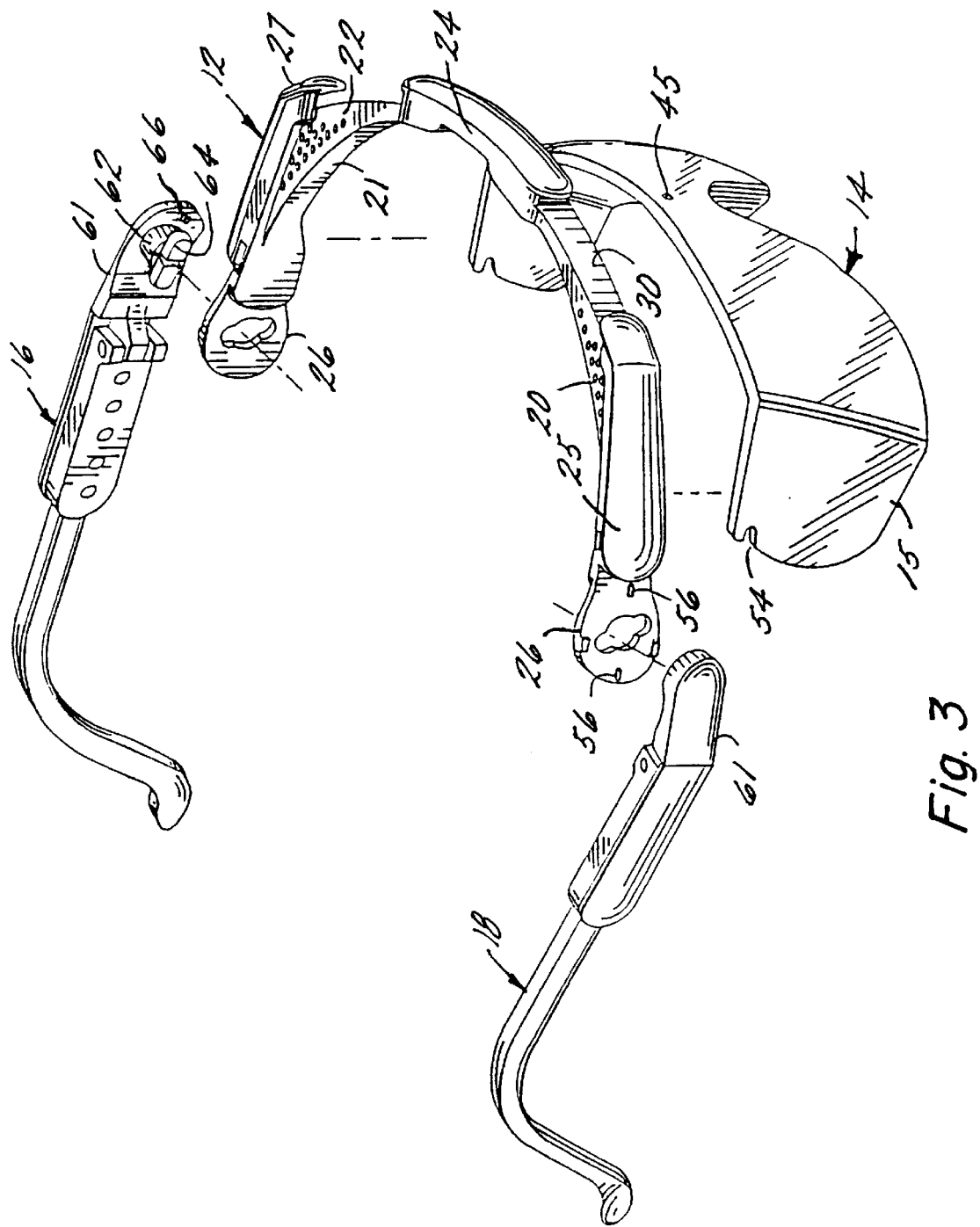
FIG. 3 is a perspective, exploded view of the eyewear of FIG. 2.
Figure 5:
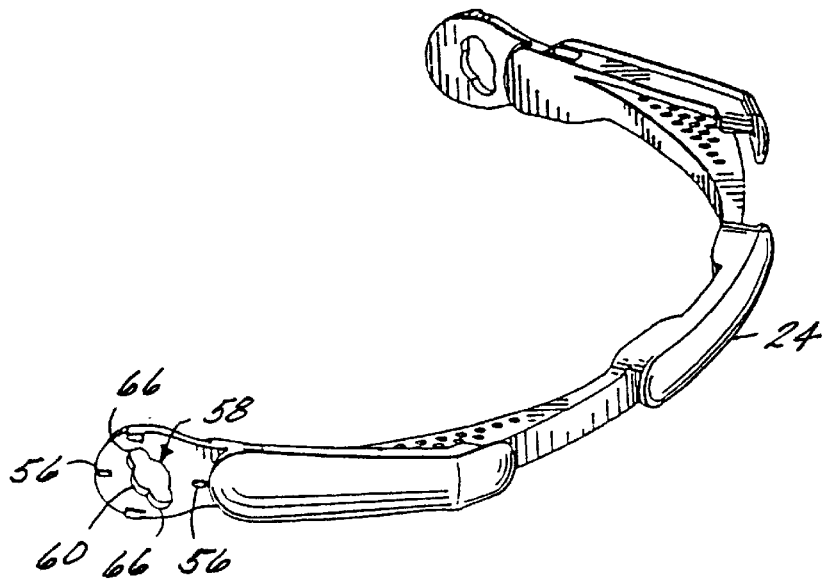
FIG. 5 is a perspective view of the ventilated browbar frame.
Figure 6:
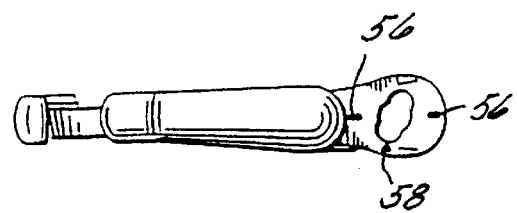
FIG. 6 is a side view of the ventilated browbar frame.
Figure 7:
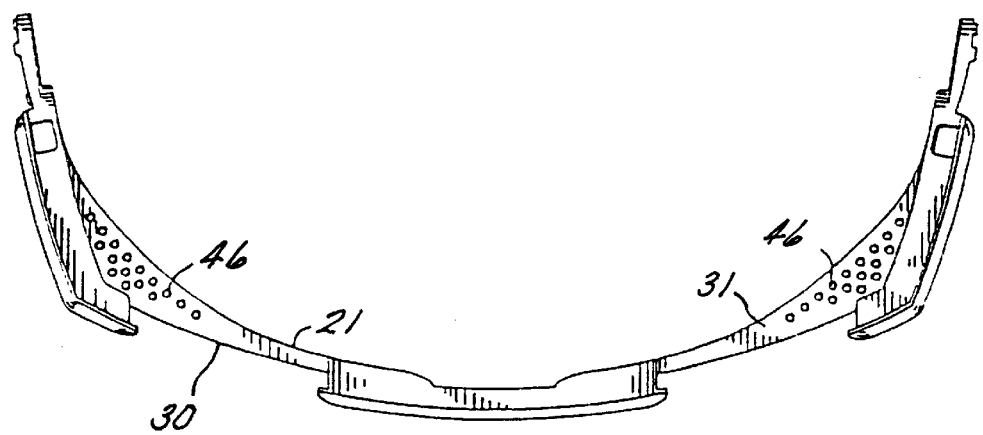
FIG. 7 is a top view of the ventilated browbar frame.
Figure 9:
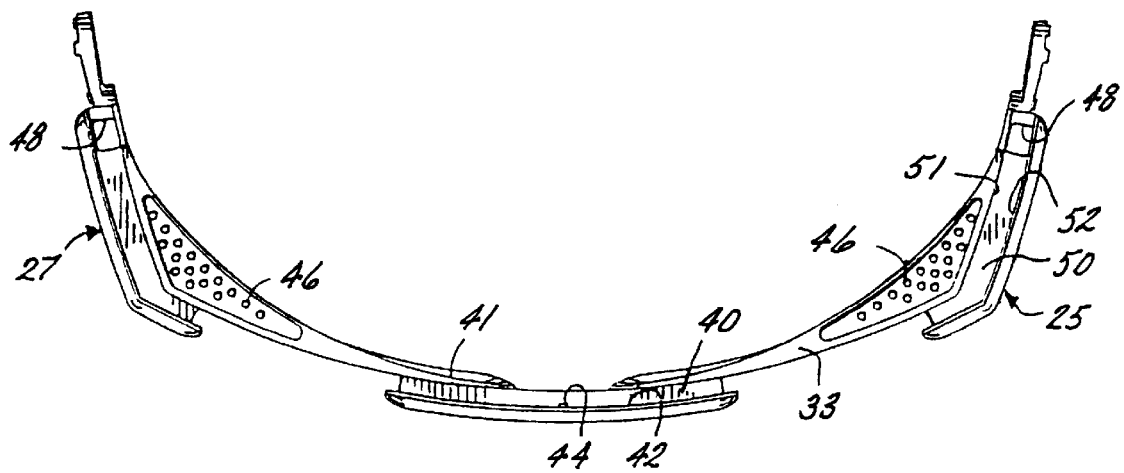
FIG. 9 is a bottom view of the ventilated browbar frame.
Figure 10:
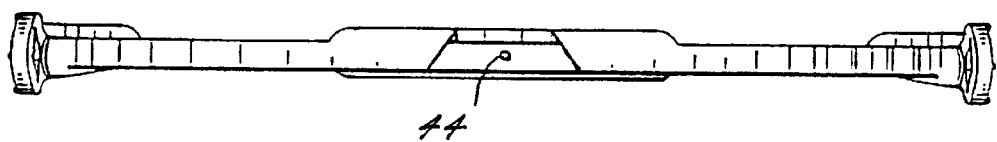
FIG. 10 is a rear view of the ventilated browbar frame.

The ventilated browbar frame 12 is preferably of a molded one-piece construction. As shown in FIG. 3, the browbar frame 12 has an inside surface 21 that is curved so as to comfortably fit against the forehead of the wearer. An outer surface 30 follows the curve of a lens 14. The browbar frame includes opposed top surface 31 (FIG. 7) and bottom surface 33 (FIG. 9). The browbar frame 12 includes a left ventilated section 20 and a right ventilated section 22. Each ventilated section includes a plurality of openings 46 (FIGS. 7 and 9) passing through the browbar frame 12 for allowing air to pass through the eyewear and prevent fogging. The openings 46 pass through top surface 31 and bottom surface 33. This allows the warm air to naturally flow upwards (warm air rising) through openings 46 drawing cool air underneath the bottom lip of lens 14. It is understood that the browbar frame 12 may have a variety of ventilated areas (e.g. ventilated along its entire length) and the invention is not limited to a left and right ventilated area as shown in FIG. 3. The browbar frame 12 includes central mounting section 24, left mounting section 25 and right mounting section 27. The central, left and right mounting sections secure the lens 14 to the browbar frame 12. As will be described below, the lens 14 is detachably secured to the browbar frame 12 to facilitate removal of the lens 14. The browbar frame 12 includes attachment segments generally shown at 26. Attachment segments 26 receive the pivotal, adjustable temple assemblies 16 and 18.

Figure 8:
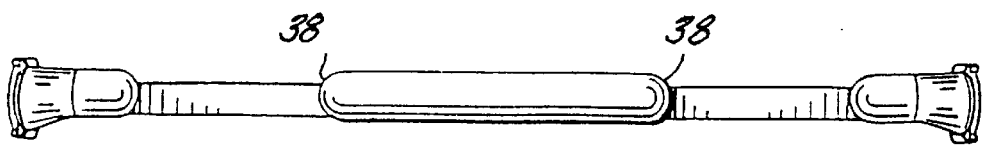
FIG. 8 is a front view of the ventilated browbar frame.

A detailed description of the browbar frame 12 is provided with reference to FIGS. 5–10. Central mounting section 24, as viewed from the front, is seen as an elongated rectangle with the ends 38 being preferably semi-circular in shape (FIG. 8). As seen in bottom view, FIG. 9, central mounting section 24 has a channel 40 which receives a portion of lens 14. Channel 40 has an outside wall 42 curved to match the outside surface of lens 14 and an inside wall 41 shaped to match the inside surface of the lens 14. Additionally, there preferably is a dimple 44 which matches and mates a hole 45 (FIG. 3) in the lens 14 to provide extra rigidity when the ventilated browbar frame 12 is secured to the lens 14.

Left mounting section 25 similarly has a channel 50 having an inside wall 51 shaped to match the inside surface of lens 14 and an outside wall shaped to match the outside surface of lens 14. Right mounting section 27 is similar to left mounting section 25. The left mounting section 25 and right mounting section 27 each include a ridge 48 for engaging detents 54 (FIG. 3) on lens 14.

Attachment segments 26 are positioned at the distal ends of the browbar frame 12 and receive the two pivotal, adjustable temple assemblies 16, 18. While any suitable temple assembly (adjustable or non-adjustable) may be used with browbar frame 12, in a preferred embodiment, the temple assemblies are adjustable and more preferably, the adjustable temple assemblies 16, 18 are the same as the adjustable temple assemblies disclosed in U.S. application Ser. No. 08/770,920 filed Dec. 20, 1996 entitled "Flexible Temple Endpiece" which is assigned to the assignee hereof, all of the contents of which are incorporated herein by reference. Of course, as mentioned, any other suitable temple or temple assembly may be substituted for the preferred temple embodiment discussed herein.

Adjustable temple assemblies 16, 18 have an end piece 61 which has formed therein a plurality of recesses 66 which are designed to engage projections 56 formed on attachment segment 26 located on both sides of mounting hole 58. Mounting hole 58 has a round center diameter 60 to accommodate the mounting post of the pivotal, adjustable temple assemblies 16, 18 which has a circular neck 62 and an oblong fastening head 64 (see FIG. 3). Mounting hole 58 has an elongation 66 on either side of round center 60 to accommodate the insertion of oblong fastening head 64. Reference is made to U.S. application Ser. No. 08/770,920 concerning detail for mounting adjustable temple assemblies 16, 18 to browbar frame 12 of the present invention.

It should be noted that the use of attachment segment 26 to connect adjustable temple assemblies 16, 18 to the browbar frame 12 allows the user to adjust the pantoscopic angle of the eyewear 10. An additional feature of adjustable temple assemblies 16, 18 is that the assemblies are hinged, allowing the adjustable temple assemblies 16, 18 to be folded towards the lens 14. This reduces the size of eyewear 10 for storage and reduces the likelihood that temples 16 and 18 will be damaged. Another advantageous feature of temple assemblies 16, 18 is that the temple tips 78 are movably mounted to the temple length adjustment housing 80 which allows the user to adjust the overall length of temple assemblies 16, 18.

Lens 14 is a conventional lens and is preferably a molded one-piece construction. Lens 14 may be a prescription lens but will preferably be a plano lens. Lens 14 may be suitably shielded (e.g., a sunglass) or be clear and when used for safety or recreational use, will be made from a suitably strong, impact resistant polymer such as polycarbonate. Lens 14 may have any suitable geometric shape such as cylindrical, spherical, toric or an aspheric shape such as parabolic or elliptical, although preferably, that portion of lens 14 between sideshields 15 will be spherical.

Attachment of the lens 14 to the browbar frame 12 will now be described. The lens detents 54 are positioned to engage the ridges 48 in the left and right mounting sections 25 and 27. The lens 14 is then moved towards the browbar frame 12 and the lens is positioned in channel 40 in central mounting section 24 and in channel 50 in the left and right mounting sections 25 and 27. The lens 14 is manipulated so that dimple 44 engages hole 45 and secures the lens 14 to the browbar frame 12.

The novel browbar frame 12 provides the assembled eyewear 10 with an appearance of being partially frameless. The partially frameless mount allows the lens 14 to wrap downwardly over the lower part of the face for further protection while sealing the area above the face with ventilated browbar frame 12. It will be appreciated that a nose piece such as disclosed in aforementioned U.S. application Ser. No. 08/770,920 may be incorporated with lens 14 to provide better fit and comfort if so desired. In addition, the temple assemblies 16 and 18 may be replaced by a strap holding temple and strap such as that disclosed in U.S. patent application Ser. No. 08/806,595 which is assigned to the assignee hereof, all of the contents of which are incorporated herein by reference.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A ventilated browbar frame and temple assembly for use in eyewear comprising:

a browbar frame including:
   an inside surface for positioning adjacent a wearer's head;
   an outside surface opposite said inside surface;
   a top surface joining said inside and outside surface;
   a bottom surface opposite said top surface;
   a ventilation opening formed through said top surface and said bottom surface;
   an attachment segment positioned at each distal end of the browbar frame; and
   a temple detachably connected to said attachment segment.

2. The ventilated browbar frame and temple assembly of claim 1 wherein said browbar frame further includes a mounting section for receiving a lens.

3. The ventilated browbar frame and temple assembly of claim 2 wherein said mounting section comprises a central mounting section having an inside wall shaped to match an inside surface of the lens and an outside wall shaped to match an outside surface of the lens.

4. The ventilated browbar frame and temple assembly of claim 3 wherein said mounting section comprises:
   a left mounting section having an inside wall shaped to match an inside surface of the lens and an outside wall shaped to match an outside surface of the lens; and
   a right mounting section having an inside wall shaped to match an inside surface of the lens and an outside wall shaped to match an outside surface of the lens.

5. The ventilated browbar frame and temple assembly of claim 4 wherein said left mounting section includes a first ridge for engaging a first detent formed in the lens and said right mounting section includes a second ridge for engaging a second detent formed in the lens.

6. The ventilated browbar frame and temple assembly of claim 2 wherein said central mounting section includes a dimple for engaging a hole in the lens.

7. The ventilated browbar frame and temple assembly of claim 2 wherein said mounting section comprises:
   a left mounting section having an inside wall shaped to match an inside surface of the lens and an outside wall shaped to match an outside surface of the lens; and
   a right mounting section having an inside wall shaped to match an inside surface of the lens and an outside wall shaped to match an outside surface of the lens.

8. The ventilated browbar frame and temple assembly of claim 7 wherein said left mounting section includes a first ridge for engaging a first detent formed in the lens and said right mounting section includes a second ridge for engaging a second detent formed in the lens.

9. The ventilated browbar frame and temple assembly of claim 1 wherein said attachment segment includes an opening therein, and said temple includes a mounting post extending therefrom, said opening for receiving said mounting post thereby detachably connecting said temple to said attachment segment.

10. The ventilated browbar frame and temple assembly of claim 9 further comprising a projection formed adjacent to said opening, said temple including a plurality of recesses for receiving said projection.

11. The ventilated browbar frame and temple assembly of claim 1 wherein said temple is pivotally mounted to said attachment segment for allowing said temple to pivot about a first axis.

12. The ventilated browbar frame and temple assembly of claim 11 wherein said temple includes a hinge for allowing said temple to pivot about a second axis.

13. Eyewear comprising:
a browbar frame including:
an inside surface for positioning adjacent a wearer's head;
an outside surface opposite said inside surface;
a top surface joining said inside and outside surface;
a bottom surface opposite said top surface;
a ventilation opening formed through said top surface and said bottom surface;
an attachment segment positioned at each distal end of the browbar frame;
a temple detachably connected to said attachment segment; and
a lens detachably secured to said browbar frame.

14. The eyewear of claim 13 wherein said browbar frame further comprises a mounting section for receiving said lens.

15. The eyewear of claim 14 wherein said mounting section comprises a central mounting section having an inside wall shaped to match an inside surface of the lens and an outside wall shaped to match an outside surface of the lens.

16. The eyewear of claim 15 wherein said central mounting section includes a dimple for engaging a hole in said lens.

17. The eyewear of claim 15 wherein said mounting section comprises:
a left mounting section having an inside wall shaped to match an inside surface of said lens and an outside wall shaped to match an outside surface of said lens; and
a right mounting section having an inside wall shaped to match an inside surface of said lens and an outside wall shaped to match an outside surface of said lens.

18. The eyewear of claim 17 wherein said left mounting section includes a first ridge for engaging a first detent formed in said lens and said right mounting section includes a second ridge for engaging a second detent formed in said lens.

19. The eyewear of claim 14 wherein said mounting section comprises:
a left mounting section having an inside wall shaped to match an inside surface of said lens and an outside wall shaped to match an outside surface of said lens; and
a right mounting section having an inside wall shaped to match an inside surface of said lens and an outside wall shaped to match an outside surface of said lens.

20. The ventilated browbar frame of claim 19 wherein said left mounting section includes a first ridge for engaging a first detent formed in the lens and said right mounting section includes a second ridge for engaging a second detent formed in the lens.

21. The eyewear of claim 13 wherein said attachment segment includes an opening therein, and said temple includes a mounting post extending therefrom, said opening for receiving said mounting post thereby detachably connecting said temple to said attachment segment.

22. The eyewear of claim 21 further comprising a projection formed adjacent to said opening.

23. The eyewear of claim 22 wherein said temple assembly includes a plurality of recesses for receiving said projection.

24. The eyewear of claim 13 wherein said temple is pivotally mounted to said attachment segment for allowing said temple to pivot about a first axis.

25. The eyewear of claim 24 wherein said temple includes a hinge for allowing said temple to pivot about a second axis.

* * * * *